(12) United States Patent
Sato

(10) Patent No.: US 10,456,304 B2
(45) Date of Patent: Oct. 29, 2019

(54) TRANSPORT UNIT AND METHOD FOR MANUFACTURING DISPOSABLE WEARING ARTICLES USING SAME

(71) Applicant: ZUIKO CORPORATION, Osaka (JP)

(72) Inventor: Hitoshi Sato, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 46 days.

(21) Appl. No.: 15/568,069

(22) PCT Filed: Mar. 30, 2016

(86) PCT No.: PCT/JP2016/060385
§ 371 (c)(1),
(2) Date: Oct. 20, 2017

(87) PCT Pub. No.: WO2016/170940
PCT Pub. Date: Oct. 27, 2016

(65) Prior Publication Data
US 2018/0140471 A1    May 24, 2018

(30) Foreign Application Priority Data

Apr. 24, 2015    (JP) ................................. 2015-089523

(51) Int. Cl.
*A61F 13/15*    (2006.01)
*D04H 1/70*    (2012.01)
*B65G 47/84*    (2006.01)

(52) U.S. Cl.
CPC .. *A61F 13/15764* (2013.01); *A61F 13/15772* (2013.01); *B65G 47/846* (2013.01); *A61F 13/15804* (2013.01); *D04H 1/70* (2013.01)

(58) Field of Classification Search
CPC ............... A61F 13/15764; A61F 13/15; A61F 13/15772; D04H 1/70
See application file for complete search history.

(56) References Cited

U.S. PATENT DOCUMENTS 4,880,102 A   11/1989   Indrebo
5,556,504 A   9/1996   Rajala et al.
(Continued)

FOREIGN PATENT DOCUMENTS

EP   1162162   12/2001
EP   3064178   9/2016
(Continued)

OTHER PUBLICATIONS

International Search Report dated Jun. 21, 2016 in International (PCT) Application No. PCT/JP2016/060385.
(Continued)

*Primary Examiner* — Mark A Osele
*Assistant Examiner* — Christopher C Caillouet
(74) *Attorney, Agent, or Firm* — Wenderoth, Lind & Ponack, L.L.P.

(57) ABSTRACT

A transport unit includes: a transporting device that turns a pad 90 degrees while the pad rotates from a receiving position to a transfer position; and first and second receiving rollers that sandwich a sheet and an absorbent body between a holding surface and the respective receiving rollers at the transfer position. The holding surface includes first and second sloped surfaces that are aligned along a pad rotating shaft which extends at the transfer position. The first and second receiving rollers have outer diameters decreasing from proximal ends to distal ends and are disposed such that the distal ends are positioned on sides of first and second ends of the holding surface, respectively. The first and second receiving rollers are disposed so as to sandwich the sheet and the absorbent body between the first and second sloped surfaces and the first and second receiving rollers, respectively.

7 Claims, 9 Drawing Sheets

(56) References Cited

U.S. PATENT DOCUMENTS

| | | |
|---|---|---|
| 6,319,347 B1 | 11/2001 | Rajala et al. |
| 6,648,122 B1 | 11/2003 | Hirsch et al. |
| 7,398,870 B2 * | 7/2008 | McCabe ........... A61F 13/15764 198/377.08 |
| 2002/0036051 A1 | 3/2002 | Rajala et al. |
| 2002/0125105 A1 | 9/2002 | Nakakado |
| 2010/0122766 A1 | 5/2010 | Yamamoto |

FOREIGN PATENT DOCUMENTS

| | | |
|---|---|---|
| JP | 2010-63716 | 3/2010 |
| JP | 2010-115427 | 5/2010 |
| WO | 88/05416 | 7/1988 |
| WO | 96/23470 | 8/1996 |

OTHER PUBLICATIONS

Extended European search report dated Aug. 14, 2018 on European application No. 16782962.1.

* cited by examiner

TRANSPORT UNIT AND METHOD FOR MANUFACTURING DISPOSABLE WEARING ARTICLES USING SAME

TECHNICAL FIELD

The present invention relates to a transport unit that conveys a first transportation object onto a second transportation object and joins the first transportation object to the second transportation object.

BACKGROUND ART

A conventional transport unit has been known that conveys a first transportation object onto a second transportation object and joins the first transportation object to the second transportation object. Patent Literature 1 discloses such a transport unit that includes a rotatable rotating drum having a suction part that holds an absorbent body by suction, which is the first transportation object, and a cylindrical roller mechanism that rotates while sandwiching the absorbent body and a web, which is the second transportation object, between the rotating drum and the cylindrical roller mechanism to join the absorbent body to the web. The rotating drum disclosed in Patent Literature 1 makes the suction part receive the absorbent body at a receiving point and then rotate to a transfer point to transfer the absorbent body onto the web at the transfer point. The suction part turns 90 degrees about a radial direction of the rotating drum while being moved from the receiving point to the transfer point, and the suction part transfers the absorbent body onto the web in a state where the absorbent body is turned 90 degrees from the orientation of the absorbent body on the suction part at the receiving point.

The outer surface of the suction part disclosed in Patent Literature 1 has, for example, sloped surfaces to receive the absorbent body smoothly at the receiving point. When the suction part is at the receiving point, the sloped surfaces are sloped radially inward toward both ends in the rotating direction of the rotating drum. As the suction part turns 90 degrees while being moved from the receiving point to the transfer point, the sloped surfaces of the outer surface of the suction part at the transfer point are sloped radially inward toward both ends in the rotational axis direction of the rotating drum.

The rotating drum disclosed in Patent Literature 1 is configured such that the sloped surfaces of the outer surface of the suction part at the transfer point are sloped radially inward toward both the ends in the rotational axis direction, which generates differences in circumferential speed on the sloped surfaces. The absorbent body disposed on the sloped surfaces is sandwiched between the sloped surfaces of the outer surface of the suction part and the outer surface of the cylindrical roller mechanism to be joined to the web. The circumferential speed on the sloped surfaces of the outer surface of the suction part varies in the rotational axis direction of the rotating drum, whereas the circumferential speed on the outer surface of the roller mechanism has no variation in the rotational axis direction of the roller mechanism. Thus, the absorbent body, which is the first transportation object, and the web, which is the second transportation object, might be joined with crinkles formed on the absorbent body or the web.

CITATION LIST

Patent Literature

Patent Literature 1: Japanese Unexamined Patent Publication No. 2010-115427 (in particular, see FIG. 7)

SUMMARY OF INVENTION

An object of the present invention is to provide a transport unit that solves the aforementioned problem, and a method for manufacturing a disposable wearing article using the transport unit.

A transport unit according to an aspect of the present invention is a transport unit that conveys a first transportation object onto a second transportation object and joins the first transportation object to the second transportation object. The transport unit includes: a transporting device including a pad rotating shaft, and a pad having a holding surface that faces radially outwardly with respect to the pad rotating shaft and is capable of holding the first transportation object, the transporting device being configured to rotate the pad about the pad rotating shaft and to turn the pad about an axis extending in a radial direction of the pad rotating shaft while the pad is rotated from a receiving position where the pad receives the first transportation object to a transfer position where the pad transfers the first transportation object onto the second transportation object; and a receiving roller that, when the pad rotates and comes to the transfer position, rotates while sandwiching the first transportation object and the second transportation object between the holding surface of the pad and the receiving roller to join the first transportation object to the second transportation object and guide the second transportation object to a predetermined direction. The holding surface includes a first sloped surface and a second sloped surface, the first sloped surface and the second sloped surface being such that, when the pad is at the transfer position, a distance from the pad rotating shaft to the first sloped surface decreases toward a first end along the pad rotating shaft, while a distance from the pad rotating shaft to the second sloped surface decreases toward a second end along the pad rotating shaft. The receiving roller includes a first receiving roller and a second receiving roller. The first receiving roller is disposed such that an outer diameter of the first receiving roller decreases from a proximal end to a distal end along a first rotational axis which is a rotation center of the first receiving roller, and the distal end of the first receiving roller is positioned on the side of the first end of the holding surface to sandwich the first transportation object and the second transportation object between the first sloped surface and the first receiving roller when the pad is at the transfer position, and the second receiving roller is disposed such that an outer diameter of the second receiving roller decreases from a proximal end to a distal end along a second rotational axis which is a rotation center of the second receiving roller, and the distal end of the second receiving roller is positioned on the side of the second end of the holding surface to sandwich the first transportation object and the second transportation object between the second sloped surface and the second receiving roller when the pad is at the transfer position.

The transport unit is capable of preventing forming of crinkles on the first transportation object or the second transportation object when joining the first transportation object to the second transportation object.

DESCRIPTION OF EMBODIMENTS

Figure 1:
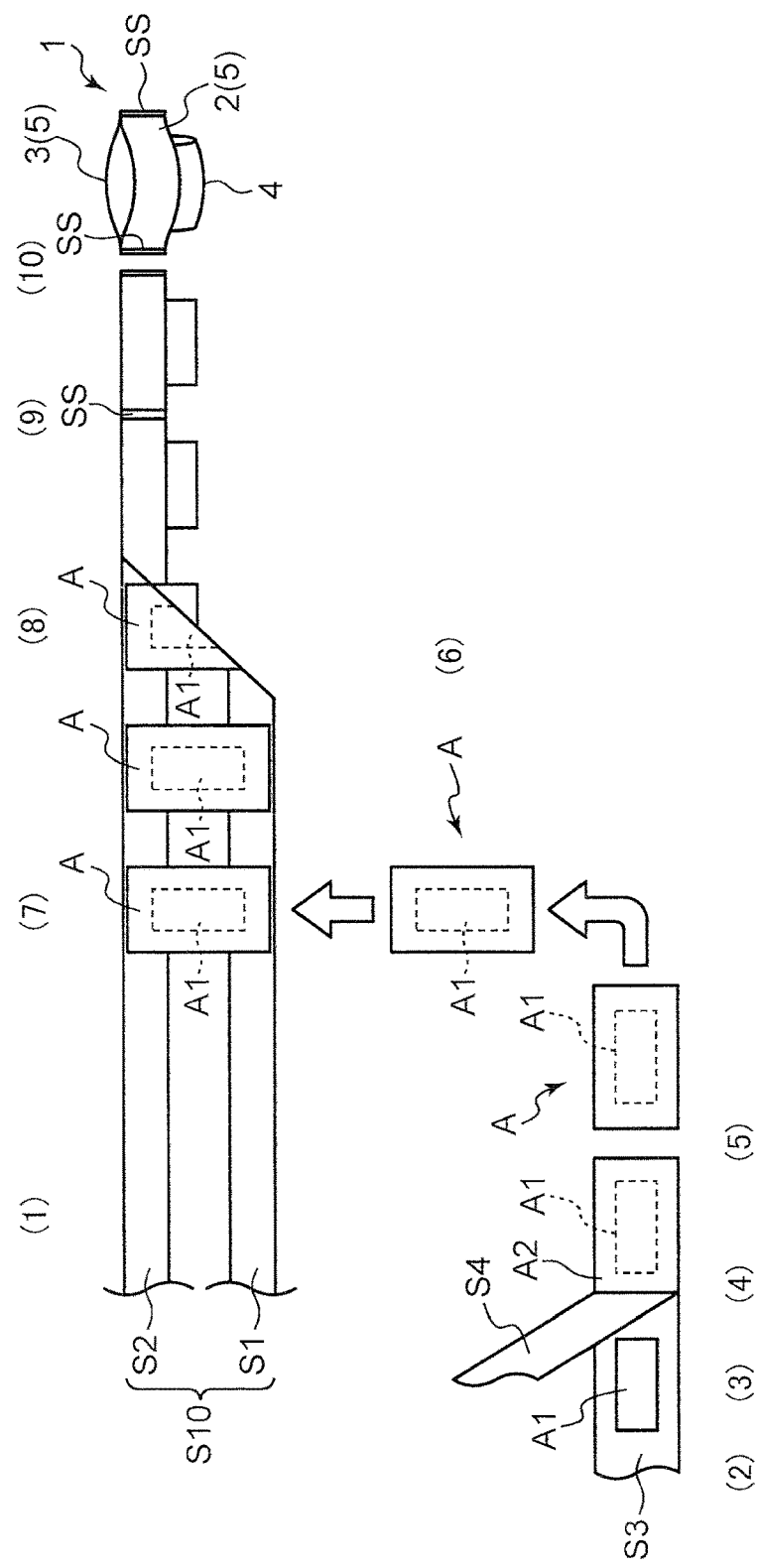
FIG. 1 is a schematic process diagram illustrating a method for manufacturing a disposable diaper according to an embodiment.

An embodiment of the present invention will now be described with reference to the drawings. For convenience of explanation, FIG. 1 referred below illustrates, in a simplified manner, only major steps among the manufacturing steps in a method for manufacturing a disposable wearing article 1 according to the embodiment. For convenience of explanation, FIGS. 2 to 9 referred below illustrate, in a simplified manner, only major components among the components of a transport unit X1 according to the embodiment. A transport unit according to the present invention and a method for manufacturing a disposable wearing article using the transport unit may include a component or a step not illustrated in the drawings referred in the description.

FIG. 1 is a process diagram illustrating a method for manufacturing a disposable diaper 1, which is an example of the disposable wearing article according to the present invention.

The disposable diaper 1 includes a front part (waist part) 2 that is to be positioned in front of the belly of a wearer, a back part (waist part) 3 that is to be positioned at the buttock of the wearer, and a crotch part 4 that is to be positioned at the crotch of the wearer.

An end of the front part 2 and an end of the back part 3 are joined together by a side seal SS. The front part 2 and the back part 3 are expandable. Specifically, the front part 2 and the back part 3 may be formed of an elastic material (elastic non-woven cloth) or by attaching a stretched elastic member between a pair of sheets made of non-woven cloth. The elastic member may be formed of polyurethane, natural rubber, or thermoplastic resin. The elastic member may have a string shape or a ribbon shape.

The crotch part 4 is joined to the front part 2 and the back part 3 so as to bridge between the front part 2 and the back part 3.

The crotch part 4 of the embodiment is formed of an absorbent body A capable of absorbing body fluid such as urine of a wearer. Specifically, the absorbent body A includes a liquid permeable top sheet S4 provided to face the skin of a wearer, a cover sheet S3 provided to face the side opposite the skin of a wearer, and an absorbent core A1 provided between the sheets S3 and S4. The body fluid permeated through the top sheet S4 is absorbed by the absorbent core A1. The top sheet S4 may be formed of non-woven cloth or a mesh sheet that allows liquid to permeate therethrough. The cover sheet S3 may be formed of a polyethylene film having air permeability, a non-woven cloth having water repellency and air permeability, or a layered sheet composed of such films or non-woven cloths. The absorbent core A1 may be formed by layering fibrillated fluffs made by crushing a roll pulp. High water-absorptive polymer may be mixed in the fluff.

The embodiment includes the crotch part 4 formed of, but not limited to, the absorbent body A. For example, the crotch part 4 not including the absorbent core A1 may be used.

The disposable diaper 1 described above includes the front part 2 and the back part 3 provided independently. The disposable diaper may not necessarily have such a configuration. For example, a sheet may have a part serving as the front part 2 and a part serving as the back part 3 and be provided with two leg holes, so that the portion of the sheet between the leg holes serve as the crotch part 4. In this case, the absorbent body A can be joined to the portion of the sheet between the leg holes.

A method for manufacturing the disposable diaper 1 will now be described with reference to FIG. 1.

The method for manufacturing the disposable diaper 1 includes a waist sheet transporting step (1), a crotch sheet transporting step (2), a core joining step (3), a sheet joining step (4), an absorbent body cutting step (5), an absorbent body joining step (6), a folding step (7), a side sealing step (8), and a cutting step (9).

In the waist sheet transporting step (1), a sheet S10, which is an example of a second transportation object according to the embodiment, is conveyed along the longitudinal direction of the sheet S10. The sheet S10 includes a front sheet (waist sheet) S1, which is an example of a first transportation element according to the present invention, and a rear sheet (waist sheet) S2, which is an example of a second transportation element according to the present invention. The front sheet S1 forms the front part 2 of the disposable diaper 1. The rear sheet S2 forms the back part 3 of the disposable diaper 1. The front sheet S1 and the rear sheet S2 are conveyed parallel with a gap therebetween. The waist sheet transporting step (1) is performed with the front sheet S1 and the rear sheet S2 given a predetermined tension until completion of the cutting step (9), which will be described later.

In the crotch sheet transporting step (2), the cover sheet S3 is conveyed along the longitudinal direction of the cover sheet S3. The direction of transporting the cover sheet S3 is parallel to the direction of transporting the front sheet S1 and the rear sheet S2. The crotch sheet transporting step (2) is performed with the cover sheet S3 given a predetermined tension until completion of the absorbent body cutting step (5), which will be described later.

In the core joining step (3), the cover sheet S3 is joined to the absorbent core A1 disposed on the cover sheet S3.

In the sheet joining step (4), the top sheet S4 is disposed on the cover sheet S3 with the absorbent core A1 between the top sheet S4 and the cover sheet S3, and the top sheet S4 is joined to the cover sheet S3 to form a continuous body of the absorbent body A (reference sign omitted).

In the absorbent body cutting step (5), the cover sheet S3 and the top sheet S4 are cut at a position between the absorbent cores A1 to cut out an absorbent body A from the continuous body. The absorbent body A is an example of the first transportation object according to the present invention.

In the absorbent body joining step (6), the absorbent body (crotch section element) A is turned 90 degrees and conveyed to a position where the absorbent body A extends from the front sheet S1 to the rear sheet S2, and an end of the absorbent body A is joined to the front sheet S1 while the other end of the absorbent body A is joined to the rear sheet S2 to form a joint assembly (reference sign omitted). In this step, for example, an adhesive is provided at a predetermined location on the front sheet S1 and the rear sheet S2 to join both the sheets S1 and S2 to the absorbent body A via the adhesive.

In the folding step (7), the joint assembly is folded in the width direction perpendicular to the longitudinal direction of the sheets S1 and S2.

In the side sealing step (8), the overlapping portions of the sheets S1 and S2 are joined on both sides with respect to the absorbent body A in the longitudinal direction of the sheets S1 and S2 to form side seals SS.

In the cutting step (9), the sheets S1 and S2 are cut so that the side seals SS remain on both the sides with respect to the absorbent body A in the longitudinal direction of the sheets S1 and S2 to form a disposable diaper 1.

In the manufacturing method described above, the absorbent body A is disposed from the front sheet S1 to the rear sheet S2, which are conveyed parallel, and then the absorbent body A is joined to the sheets S1 and S2. The manufacturing method according to the present invention is not limited to the steps described above.

For example, in the waist sheet transporting step (1), a waist sheet having parts serving as the front part 2 and the back part 3 may be transported. In this case, a plurality of leg holes is formed in the waist sheet, and thus a portion serving as the crotch part 4 is formed between the leg holes in the waist sheet. In the absorbent body joining step (6), the absorbent body A is joined to the portion between the leg holes in the waist sheet.

Figure 2:
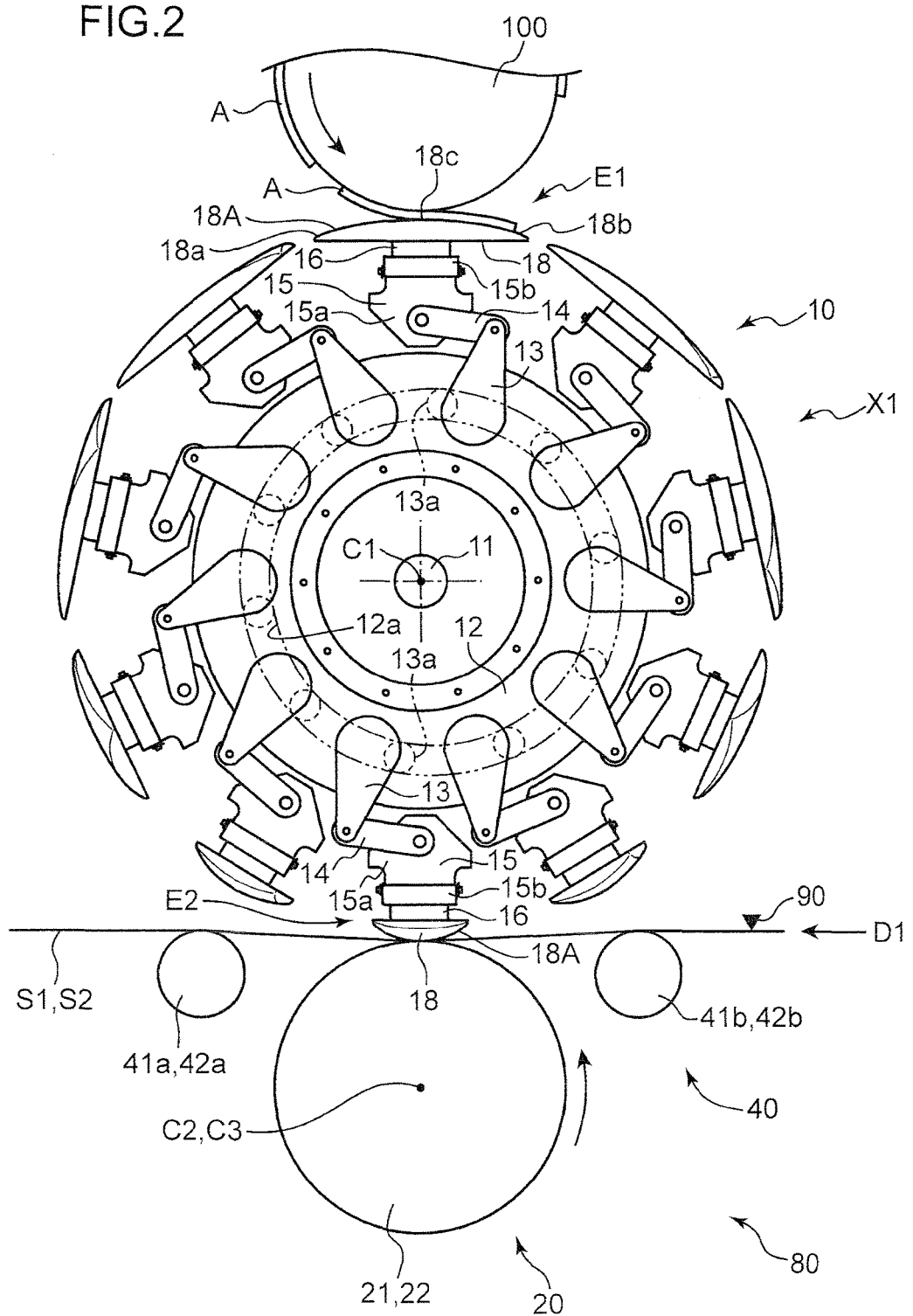
FIG. 2 is a front view illustrating a schematic configuration of a transport unit and a transfer roller according to the embodiment, where two of a plurality of pads are respectively at a receiving position and a transfer position.

A transfer roller 100 and a transport unit X1 used for performing the absorbent body joining step (6) will now be described below with reference to FIG. 2. FIG. 2 is a front view illustrating a schematic configuration of the transfer roller 100 and the transport unit X1.

The transfer roller 100 transfers the absorbent body A formed in the absorbent body cutting step (5) to a transporting device 10. A plurality of absorbent bodies A is attached to the outer surface of the transfer roller 100. The absorbent bodies A are placed evenly spaced apart along the circumferential direction of the transfer roller 100. The transfer roller 100 transfers the absorbent body A to a pad 18 of the transporting device 10, which will be described later, as the transfer roller 100 and the transporting device 10 rotates. The transfer is performed when the pad 18 is at a receiving position E1.

The transport unit X1 includes the transporting device 10 that receives the absorbent body A from the transfer roller 100 and conveys the absorbent body A, a receiving unit 80 that joins the absorbent body A, conveyed by the transporting device 10, to the sheets S1 and S2, and applying means 90 that applies an adhesive onto the sheets S1 and S2.

A schematic configuration of the transporting device 10 of the transport unit X1 will be described below with reference to FIG. 2.

The transporting device 10 includes a pad rotating shaft 11, and a plurality of pads 18 provided, evenly spaced apart, along the circumferential direction of the pad rotating shaft 11. The transporting device 10 of the embodiment is provided with ten pads 18.

The transporting device 10 rotates the pad rotating shaft 11 about a pad rotational axis C1 to rotate the pads 18 about the pad rotating shaft 11. The pad 18 rotating about the pad rotating shaft 11 receives the absorbent body A from the transfer roller 100 at the receiving position E1 and transfers the absorbent body A onto the sheets S1 and S2 transported between the transporting device 10 and the receiving unit 80, at the transfer position E2.

The transporting device 10 turns the pad 18 90 degrees about an axis extending in a radial direction of the pad rotating shaft 11 while the pad 18 rotates from the receiving position E1 to the transfer position E2. That is, at the transfer position E2, the transporting device 10 transfers the absorbent body A, which has been turned around 90 degrees after being received by the pad 18 at the receiving position E1, onto the sheets S1 and S2.

In the embodiment, the pad 18 is turned 90 degrees about an axis extending in a radial direction of the pad rotating shaft 11 while the pad 18 is rotated from the receiving position E1 to the transfer position E2. The present invention is not limited to the embodiment. The turning angle of the pad may suitably be changed depending on the use mode of the transporting device 10. The pad 18 may transfer the absorbent body A with a suitable orientation to the sheets S1 and S2 by being turned a predetermined angle while rotating the receiving position E1 to the transfer position E2.

Figure 3:
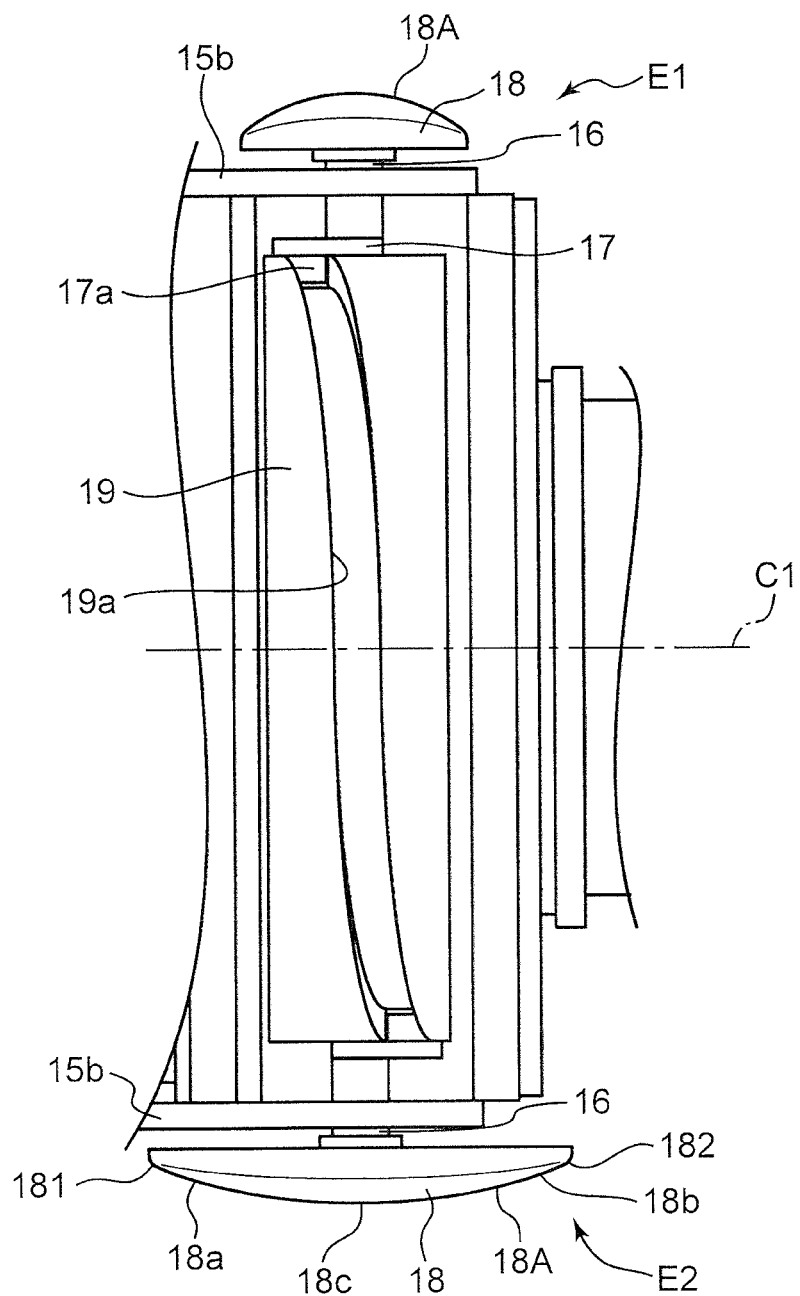
FIG. 3 is a side view illustrating a schematic configuration of a transporting device according to the embodiment.

A specific configuration of the transporting device 10 will now be described with reference to FIG. 3 as well as FIG. 2. FIG. 3 is a side view of the transporting device 10 illustrating a portion that contributes to turning the pad 18.

The transporting device 10 includes not only the pad rotating shaft 11 and the pads 18 described above but a fixed drum (not shown) provided to surround the pad rotating shaft 11, a speed adjusting cam 12 that is fixed on the distal end of the fixed drum and used to adjust the speed of the pad 18 rotating about the pad rotating shaft 11, a turning cam 19 that is fixed to the outer circumferential surface of the fixed drum and used for turning the pad 18 about the axis extending in a radial direction of the pad rotating shaft 11, and a rotating mechanism that rotates the pad 18 as the pad rotating shaft 11 rotates. The rotating mechanism includes an arm 13, a link lever 14, a driving base 15, a turning shaft 16, and a lever 17. With the arm 13 coupled to the speed adjusting cam 12 and the lever 17 coupled to the turning cam 19, the speed of the pad 18 in the circumferential direction of the pad rotating shaft 11 is adjusted and the pad 18 is turned about an axis extending in a radial direction of the pad rotating shaft 11.

The pad rotating shaft 11 is rotatable about the pad rotational axis C1. The transporting device 10 is disposed such that the pad rotational axis C1 of the pad rotating shaft 11 is parallel to the rotational axis of the transfer roller 100.

The fixed drum has a cylindrical shape with its central axis on the pad rotational axis C1. The pad rotating shaft 11 penetrates the fixed drum and the turning cam 19 and is rotatably supported by the fixed drum and the turning cam 19 via bearings. The fixed drum cannot rotate because the fixed drum is fixed to a surface on which the transporting device 10 is set. Thus, the pad rotating shaft 11 can rotate, relative to the fixed drum, inside the fixed drum.

The speed adjusting cam 12 is fixed on the distal end of the cylindrical fixed drum so as to plug the opening on the distal end. A cam groove 12a is provided in the outer surface of the speed adjusting cam 12. As illustrated in FIG. 2, the cam groove 12a has an approximately circular shape that is provided eccentric to the pad rotational axis C1.

The arm 13 is indirectly coupled to the pad rotating shaft 11 via a disk-shaped member (see FIG. 2) so as to be rotatable about the pad rotating shaft 11 as the pad rotating shaft 11 rotates. The arm 13 is coupled to the disk-shaped member so as to be rotatable about an axis parallel to the pad rotational axis C1. In the embodiment, ten arms 13 are provided corresponding to the ten pads 18. Each atm 13 extends in the direction perpendicular to the pad rotational axis C1. A cam follower 13a is provided on the proximal end of each arm 13. The cam follower 13a is shifted from the rotational axis of the arm 13. The cam follower 13a is inserted in the cam groove 12a of the speed adjusting cam 12 so as to be rotatable about an axis parallel to the pad rotational axis C1.

The link lever 14 extends from the distal end of the arm 13 in a direction perpendicular to the pad rotational axis C1 and intersecting the direction in which the arm 13 extends. Ten link levers 14 are provided corresponding to the ten arms 13. The proximal end of each link lever 14 is coupled to the distal end of the aim 13 so as to be rotatable about an axis parallel to the pad rotational axis C1.

The driving base 15 includes an external wall 15b provided in the outer side of the arm 13 and the link lever 14 with respect to a radial direction of the pad rotational axis C1, and a supported portion 15a protruding from the external wall 15b to the inner side in the radial direction. The supported portion 15a is coupled to the distal end of the link lever 14 so as to be rotatable about an axis parallel to the pad rotational axis C1. The driving base 15 rotates along a circumference of the pad rotational axis C1.

The turning cam 19 has a cylindrical shape with its central axis on the pad rotational axis C1. The turning cam 19 is fixed to the outer circumferential surface of the fixed drum so as to surround the fixed drum. The turning cam 19 is positioned in further inner side than the external wall 15b of the driving base 15 with respect to the radial direction of the pad rotational axis C1. A cam groove 19a is provided in the external surface of the turning cam 19. As illustrated in FIG. 3, the cam groove 19a is formed to encircle the pad rotational axis C1. The location in the cam groove 19a with respect to the pad rotational axis C1 changes along the circumferential direction of the pad rotational axis C1.

The turning shaft 16 extends in a radial direction of the pad rotational axis C1 to penetrate the external wall 15b of the driving base 15. The turning shaft 16 is supported by the external wall 15b so as to be rotatable about an axis along a radial direction of the pad rotational axis C1. A cam follower 17a is provided via the lever 17 on the inner end, with respect to the radial direction, of the turning shaft 16. The lever 17 extends in the direction perpendicular to the turning shaft 16. The cam follower 17a is in a position shifted from the rotational axis of the turning shaft 16. The cam follower 17a is inserted in the cam groove 19a of the turning cam 19 so as to be rotatable about an axis perpendicular to the pad rotational axis C1.

The pad 18 is coupled to the outer end, with respect to a radial direction of the pad rotational axis C1, of the turning shaft 16. In the embodiment, the pad 18 has an approximately rectangular shape extending in one direction in a plan view. As illustrated in FIG. 2, the pad 18 is positioned such that the longitudinal direction and the rotational direction of the pad 18 are parallel to each other at the receiving position E1. The pad 18 is positioned such that the lateral direction and the rotational direction of the pad 18 are parallel to each other at the transfer position E2. That is, the longitudinal direction of the pad 18 is parallel to the pad rotational axis C1 at the transfer position E2.

The pad 18 has a holding surface 18A on which the absorbent body A is held. The holding surface 18A faces radially outwardly with respect to the pad rotating shaft 11. The holding surface 18A is positioned to face the transfer roller 100 at the receiving position E1 to receive the absorbent body A from the transfer roller 100. The holding surface 18A is positioned to face the receiving roller 20 at the transfer position E2 to transfer the absorbent body A onto the sheets S1 and S2 conveyed between the holding surface 18A and the receiving roller 20.

Figure 4:
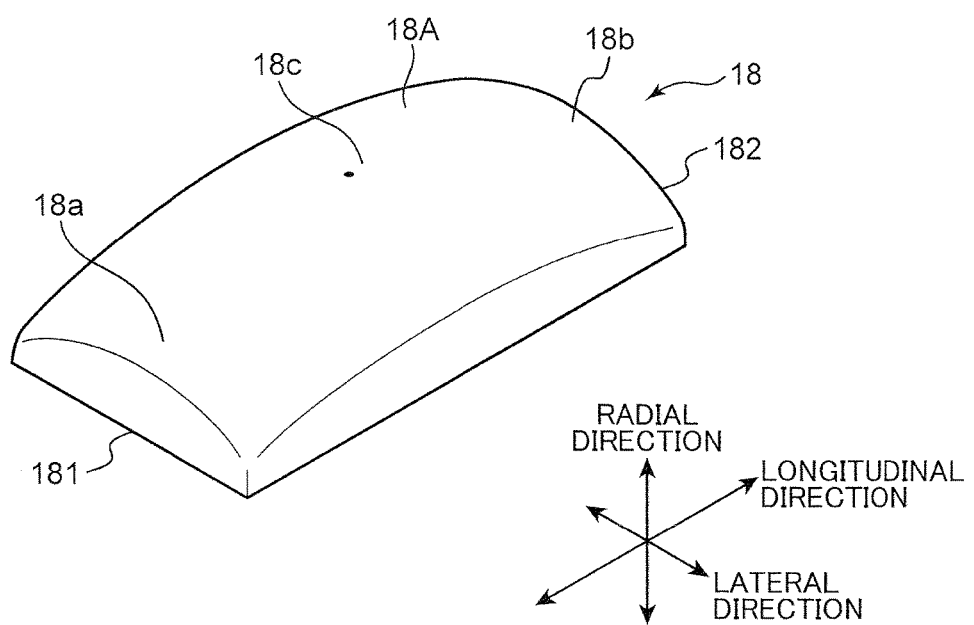
FIG. 4 is a perspective view illustrating a schematic configuration of a pad of the transporting device according to the embodiment.

As illustrated in FIG. 4, both ends, in the longitudinal direction of the pad 18, of the holding surface 18A are a first end 181 and a second end 182. With respect to the longitudinal direction of the pad, the holding surface 18A has a first sloped surface 18a positioned on the side of the first end 181, a second sloped surface 18b positioned on the side of the second end 182, and a middle surface 18C located between the first sloped surface 18a and the second sloped surface 18b. In the embodiment, the holding surface 18A has an arc shape protruding to radially outwardly with respect to the pad rotating shaft 11 when viewed along the lateral direction of the pad 18. The first sloped surface 18a, the middle surface 18c, and the second sloped surface 18b continues in this order in the longitudinal direction of the pad 18.

In the embodiment, the holding surface 18A has a spherical shape. Thus, the holding surface 18A also has an arc shape protruding to radially outwardly with respect to the pad rotating shaft 11 when viewed in the longitudinal direction of the pad 18.

Figure 5:
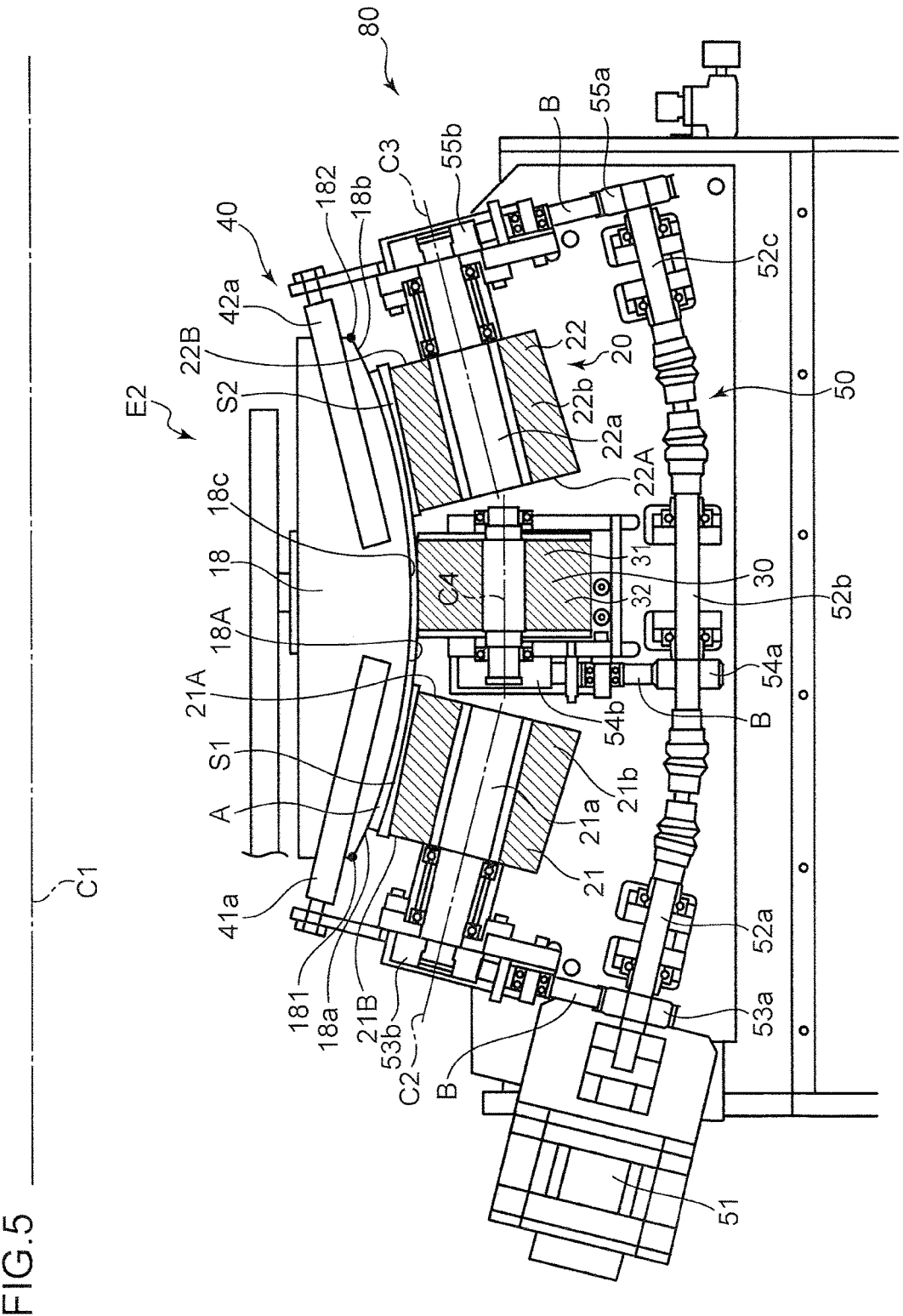
FIG. 5 is a side view illustrating a schematic configuration of a pad and a receiving unit, where the pad is at the transfer position.

FIG. 5 is a side view illustrating the pad 18 at the transfer position E2 viewed in a direction perpendicular to the pad rotational axis C1 of the pad rotating shaft 11. The longitudinal direction of the pad 18 is parallel to the pad rotational axis C1 at the transfer position E2. As illustrated in FIG. 5, at the transfer position E2, the distance from the pad rotational axis C1 to the first sloped surface 18a of the holding surface 18A decreases toward the first end 181 in the direction of the pad rotational axis C1. At the transfer position E2, the distance from the pad rotational axis C1 to the second sloped surface 18b of the holding surface 18A decreases toward the second end 182 in the direction of the pad rotational axis C1. At the transfer position E2, the middle surface 18c of the holding surface 18A is farther from the pad rotational axis C1 than the first sloped surface 18a and the second sloped surface 18b.

The transporting device 10 is configured such that the arm 13, the link lever 14, and the driving base 15 rotate as the pad rotating shaft 11 rotates, and thereby the turning shaft 16 supported by the external wall 15b of the driving base 15 and the pad 18 mounted on the turning shaft 16 turn about the pad rotating shaft 11. The arm 13 rotates about an axis parallel to the pad rotational axis C1 by the cam follower 13a inserted in the cam groove 12a in the speed adjusting cam 12 moving along the cam groove 12a. The lever 17 coupled to the turning shaft 16 rotates about an axis extending in a radial direction of the pad rotational axis C1 by the cam follower 17a inserted in the cam groove 19a in the turning cam 19 moving along the cam groove 19a. While the pad 18 rotates about the pad rotational axis C1, the rotational speed of the pad 18 is adjusted and the pad 18 turns about the axis extending in a radial direction of the pad rotational axis C1. The pad 18 is turned 90 degrees while being moved from the receiving position E1 to the transfer position E2 so that the longitudinal direction of the pad 18 becomes parallel to the rotational direction at the receiving position E1 and the lateral direction of the pad 18 becomes parallel to the rotational direction at the transfer position E2.

Figure 6:
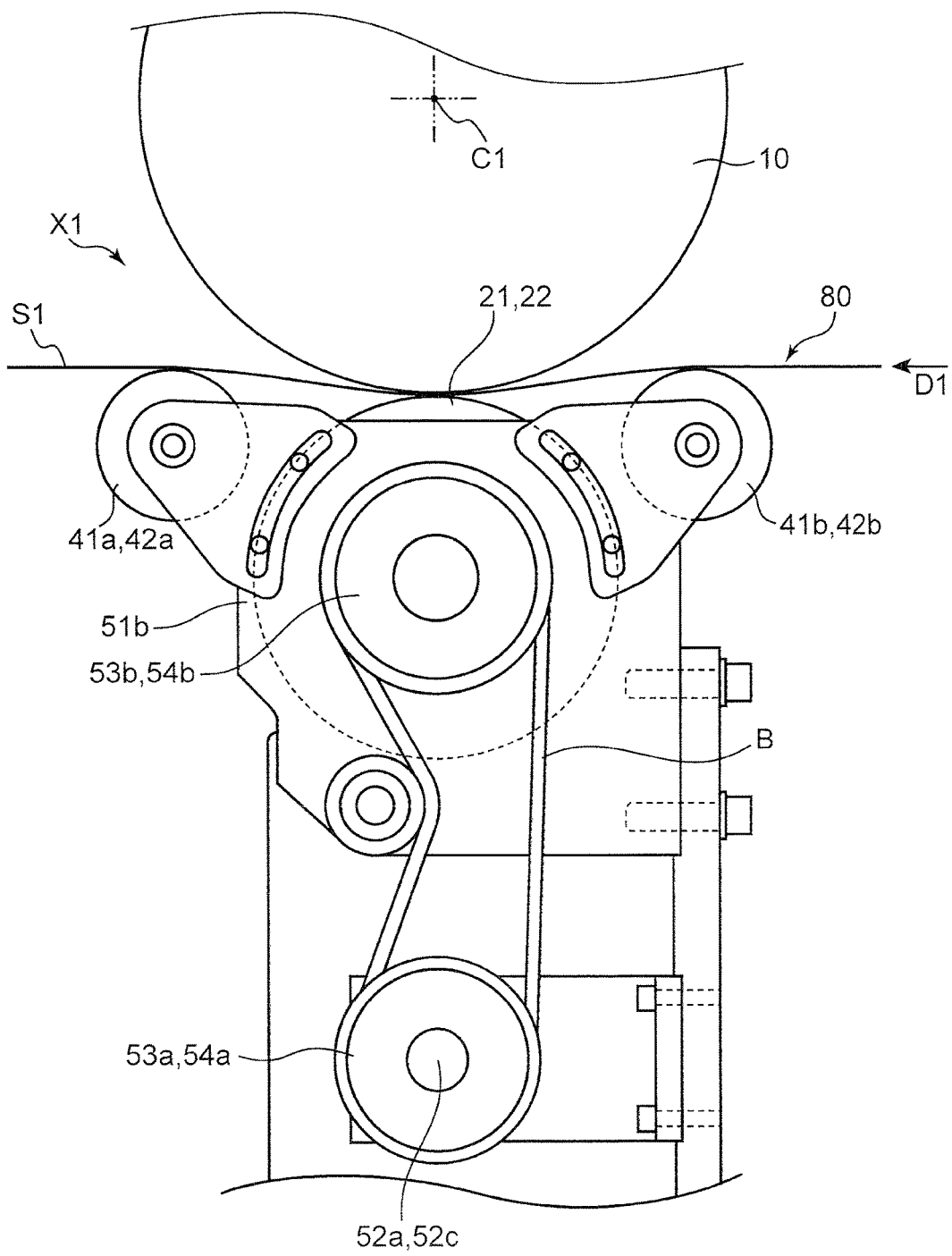
FIG. 6 is a front view illustrating a schematic configuration of a receiving unit according to the embodiment.

A schematic configuration of a receiving unit 80 of the transport unit X1 will now be described below with reference to FIGS. 2, 5, and 6. FIG. 5 is a side view illustrating the pad 18 and an essential portion of the receiving unit 80 at the receiving position E1, viewed in a direction perpendicular to the pad rotational axis C1. FIG. 6 is a front view illustrating a schematic configuration of the receiving unit 80. The transporting device 10 is illustrated in a simplified manner in FIG. 6.

As illustrated in FIG. 2, the receiving unit 80 is disposed on the side opposite to the transporting device 10 with respect to the sheets S1 and S2 between the receiving unit 80 and the transporting device 10. The sheets are transported in a transporting direction D1 perpendicular to the pad rotational axis C1. In the embodiment, the receiving position E1 and the transfer position E2 are shifted by 180 degrees about the pad rotational axis C1. The receiving unit 80 is disposed to face the transfer roller 100 with the transporting device 10 between the receiving unit 80 and the transfer roller 100.

As illustrated in FIGS. 2, 5, and 6, the receiving unit 80 includes a receiving roller 20 that joins the absorbent body A to the sheets S1 and S2 at the transfer position E2, auxiliary rollers 30 that help the joining, a guide mechanism 40 that guides the sheets S1 and S2 to be transported, and a driving mechanism 50 that rotates the receiving roller 20 and the auxiliary rollers 30 altogether.

As illustrated in FIG. 2, the receiving roller 20 is disposed so as to sandwich the sheets S1 and S2 between the holding surface 18A of the pad 18 and the receiving roller 20 at the transfer position E2. As illustrated in FIG. 6, the receiving roller 20 includes a first receiving roller 21 and a second receiving roller 22 disposed in a direction in which the pad rotational axis C1 extends.

Figure 7:
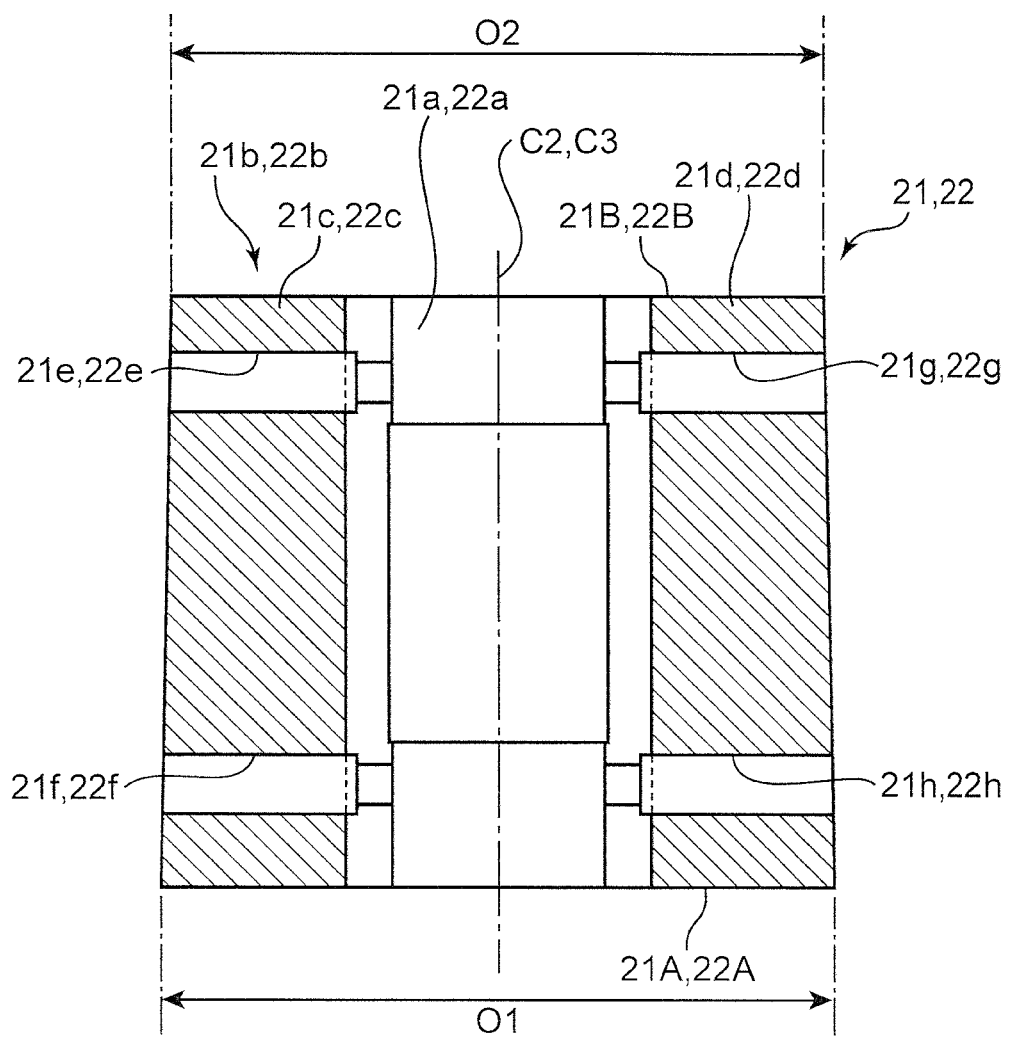
FIG. 7 is a sectional view, taken along a plane including an axis, illustrating a schematic configuration of a first receiving roller among receiving rollers according to the embodiment.
Figure 8:
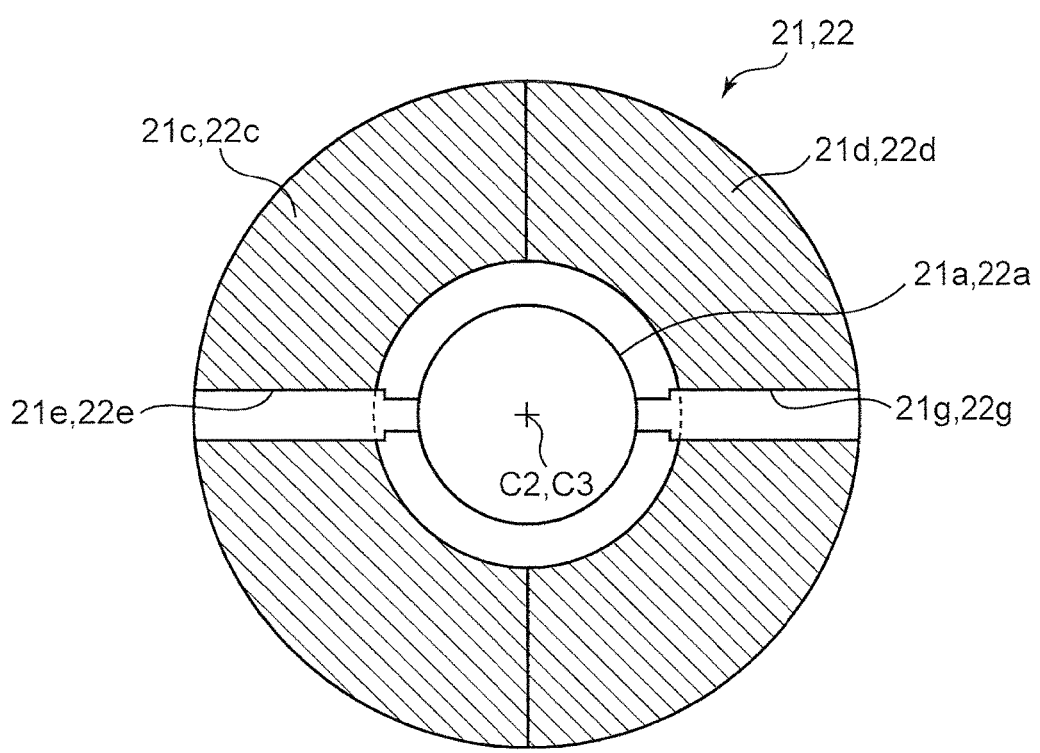
FIG. 8 is a sectional view, taken along a plane perpendicular to an axis, illustrating a schematic configuration of a first receiving roller among receiving rollers according to the embodiment.

The first receiving roller 21 and the second receiving roller 22 have the same configuration. The first and second receiving rollers 21 and 22 will now be described specifically below with reference to FIGS. 7 and 8. FIG. 7 is a sectional view of the first and second receiving rollers 21 and 22 in a plane including first and second rotational axes C2 and C3, which are rotation centers of the first and second receiving rollers 21 and 22, respectively. FIG. 8 is a sectional view of the first receiving roller 21 (second receiving roller 22) in a plane perpendicular to the first rotational axis C2 (second rotational axis C3).

As illustrated in FIGS. 7 and 8, the first and second receiving rollers 21 and 22 include shaft members 21a and 22a and outer circumferential members 21b and 22b, respectively. The outer circumferential members 21b and 22b are made of a relatively soft material, such as polyurethane foam.

The shaft members 21a and 22a extend along the first and second rotational axes C2 and C3, which are rotation centers of the first and second receiving rollers 21 and 22, respectively. The shaft members 21a and 22a are rotatable about the first and second rotational axes C2 and C3, respectively.

The outer circumferential member 21b (22b) is provided to surround the shaft member 21a (22a). The outer circumferential member 21b (22b) rotates about the first rotational axis C2 (second rotational axis C3) as the shaft member 21a (22a) rotates. The outer circumferential member 21b (22b) has a cylindrical shape having a thickness gradually decreasing from a proximal end 21A (22A) to a distal end 21B (22B) of the first receiving roller 21 (second receiving roller 22) along the direction in which the first rotational axis C2 (second rotational axis C3) extends. The shaft member 21a (22a) is disposed inside the outer circumferential member 21b (22b). An outer diameter O2 of the distal end 21B (22B) of the first receiving roller 21 (second receiving roller 22) is smaller than an outer diameter O1 of the proximal end 21A (22A) of the first receiving roller 21 (second receiving roller 22).

As illustrated in FIG. 8, the outer circumferential member 21b (22b) includes a first member 21c (22c) and a second member 21d (22d) that are divided by a plane including the first rotational axis C2 (second rotational axis C3). In the embodiment, the shape of the first member 21c (22c) and the shape of the second member 21d (22d) are plane symmetric about the plane including the first rotational axis C2 (second rotational axis C3). The shaft member 21a (22a) is circumferentially surrounded by the first member 21c (22c) and the second member 21d (22d).

The first member 21c (22c) is provided with a first through hole 21e (22e) and a first through hole 21f (22f) that penetrate the first member 21c (22c) in a radial direction of the first rotational axis C2 (second rotational axis C3). The first through hole 21e (22e) and the first through hole 21f (22f) are arranged in the direction in which the first rotational axis C2 (second rotational axis C3) extends. The first member 21c (22c) is detachably attached on the shaft member 21a (22a) by fixing fastening members (not shown) such as bolts or the like inserted in the first through hole 21e (22e) and the first through hole 21f (220 to the shaft member 21a (22a). The first member 21c (22c) is attached on one of sides in a direction perpendicular to the first rotational axis C2 (second rotational axis C3).

The second member 21d (22d) is provided with a second through hole 21g (22g) and a second through hole 21h (22h) that penetrate the second member 21d (22d) in the radial direction of the first rotational axis C2 (second rotational axis C3). The second through hole 21g (22g) and the second through hole 21h (22h) are arranged in the direction in which the first rotational axis C2 (second rotational axis C3) extends. The second member 21d (22d) is detachably attached on the shaft member 21a (22a) by fixing fastening members (not shown) such as bolts or the like inserted in the second through hole 21g (22g) and the second through hole 21h (22h) to the shaft member 21a (22a). The second member is attached on the other side in the direction perpendicular to the first rotational axis C2 (second rotational axis C3).

The first member 21c (22c) and the second member 21d (22d) may not be attached on the shaft member 21a (22a) by bolts or the like. For example, the first member 21c (22c) and the second member 21d (22d) may be attached on the shaft member 21a (22a) by inserting a portion of the first member 21c (22c) and a portion of the second member 21d (22d) in recesses formed in the outer circumferential surface of the shaft member 21a (22a). That is, the first member 21c (22c) and the second member 21d (22d) are detachably attached, by a variety of means, on the shaft member 21a (22a) on both sides in a direction intersecting the first rotational axis C2 (second rotational axis C3).

As illustrated in FIG. 5, the first receiving roller 21 is disposed such that the distal end 21B is positioned on the side of the first end 181 of the holding surface 18A of the pad 18 at the transfer position E2 and the first sloped surface 18a faces the outer circumferential surface of the outer circumferential member 21b. Specifically, the first receiving roller 21 is disposed such that the first rotational axis C2 of the first receiving roller 21 inclines along the inclination of the first sloped surface 18a with respect to the pad rotational axis C1 of the transporting device 10.

As illustrated in FIG. 5, the second receiving roller 22 is disposed such that the distal end 22B is positioned on the side of the second end 182 of the holding surface 18A of the pad 18 at the transfer position E2 and the second sloped surface 18b faces the outer circumferential surface of the outer circumferential member 22b. Specifically, the second receiving roller 22 is disposed such that the second rotational axis C3 of the second receiving roller 22 inclines along the inclination of the second sloped surface 18b with respect to the pad rotational axis C1 of the transporting device 10.

The auxiliary roller 30 includes a shaft member 31 that extends along a third rotational axis C4 which is a rotation center of the auxiliary roller 30 and is rotatable about the third rotational axis C4, and an outer circumferential member 32 that circumferentially surrounds the shaft member 31 and rotates with rotation of the shaft member 31. The auxiliary roller 30 is disposed between the first receiving roller 21 and the second receiving roller 22, in a direction of the pad rotational axis C1. The auxiliary roller 30 is disposed such that the third rotational axis C4 of the auxiliary roller 30 is parallel to the pad rotational axis C1. Accordingly, the outer circumferential surface of the outer circumferential member 32 of the auxiliary roller 30 faces the middle surface 18c of the pad 18 at the transfer position E2.

An adhesive is applied by the applying means 90 on the sheets S1 and S2 transported in the transporting direction D1. The adhesive is applied in the upstream of the transfer position E2 along the transporting direction D1. At the transfer position E2, the front sheet S1 and the absorbent body A on the first sloped surface 18a are sandwiched between the first sloped surface 18a and the outer circumferential member 21b of the first receiving roller 21, and thereby the front sheet S1 and the absorbent body A are joined via the adhesive. The rear sheet S2 and the absorbent body A on the second sloped surface 18b are sandwiched between the second sloped surface 18b and the outer circumferential member 22b of the second receiving roller 22, and thereby the rear sheet S2 and the absorbent body A are joined via the adhesive. The absorbent body A positioned at the middle surface 18c is sandwiched between the middle surface 18c and the auxiliary roller 30 when the sheets S1 and S2 and the absorbent body A are joined. In this manner, the front sheet S1 and the rear sheet S2 are connected by the absorbent body A and transported to the downstream of the transporting direction D1.

In the embodiment, the adhesive is applied on target portions on the sheets S1 and S2 by the applying means 90. However, the adhesive may be applied on a target portion on the absorbent body A by the applying means 90.

The driving mechanism 50 includes a driving unit 51, pulleys 52a, 52b, and 52c that are rotated by the driving force of the driving unit 51, first belt rollers 53a and 53b, second belt rollers 54a and 54b, third belt rollers 55a and 55b, and a plurality of belts B running about the belt rollers. The first, second, and third belt rollers are respectively provided for the pulleys 52a, 52b, and 52c.

The pulleys 52a, 52b, and 52c are mutually connected along the pad rotational axis C1 and are each supported by a supporting plate (reference sign not appended) so as to be rotatable about an axis. The driving unit 51 is mounted on the distal end of the pulley 52a. The pulley 52a is rotated by the driving force of the driving unit 51 and thereby the other pulleys 52b and 52c are rotated.

The first belt rollers 53a and 53b are provided for the pulley 52a. The first belt roller 53a is fixed to the pulley 52a. The first belt roller 53b is away from the first belt roller 53a in a direction intersecting the pad rotational axis C1 and is rotatably supported by the supporting plate (reference sign not appended). The shaft member 21a of the first receiving roller 21 is fixed to the first belt roller 53b. The belt B runs around the first belt roller 53a and the first belt roller 53b.

The second belt rollers 54a and 54b are provided for the pulley 52b. The second belt roller 54a is fixed to the pulley 52b. The second belt roller 54b is away from the second belt roller 54a in a direction intersecting the pad rotational axis C1 and is rotatably supported by the supporting plate (reference sign not appended). The shaft member 31 of the auxiliary roller 30 is fixed to the second belt roller 54b. The belt B runs around the second belt roller 54a and the second belt roller 54b.

The third belt rollers 55a and 55b are provided for the pulley 52c. The third belt roller 55a is fixed to the pulley 52c. The third belt roller 55b is away from the third belt roller 55a in a direction intersecting the pad rotational axis C1 and is rotatably supported by the supporting plate (reference sign not appended). The shaft member 22a of the second receiving roller 22 is fixed to the third belt roller 55b. The belt B runs around the third belt roller 55a and the third belt roller 55b.

The driving mechanism 50 is configured such that the driving unit 51 simultaneously rotates the pulleys 52a, 52b, and 52c to rotate the first, second, and third belt rollers 53a, 54a, and 55a attached to the pulleys 52a, 52b, and 52c, respectively, and thereby the first, second, and third belt rollers 53b, 54b, and 55b rotate via the belts B. In this manner, the first receiving roller 21, the second receiving roller 22, and the auxiliary roller 30 rotate altogether.

The guide mechanism 40 includes a pair of first guide rollers 41a and 41b that guide the front sheet S1 to be conveyed in the transporting direction D1, and a pair of second guide rollers 42a and 42b that guide the rear sheet S2 to be conveyed in the transporting direction D1.

As illustrated in FIGS. 5 and 6, the first guide rollers 41a and 41b are separately disposed from each other in the transporting direction D1 with the first receiving roller 21 between the first guide rollers 41a and 41b. The first guide rollers 41a and 41b are rotatably mounted on a support-plate (reference sign not appended) that supports the driving mechanism 50. The first guide rollers 41a and 41b are disposed closer to the pad rotational axis C1 of the transporting device 10 than the first receiving roller 21 is, in the direction perpendicular to the transporting direction D1.

For convenience of explanation, FIG. 5 illustrates the entire portion of the first guide roller 41a closer to the pad rotational axis C1 than the first receiving roller 21. However, actually, the first guide roller 41a partially overlaps the first receiving roller 21 when viewed in the transporting direction D1 as illustrated in FIG. 6. The same can be said for the first guide roller 41b.

As illustrated in FIGS. 5 and 6, the second guide rollers 42a and 42b are separately disposed from each other in the transporting direction D1 with the second receiving roller 22 between the second guide rollers 42a and 42b. The second guide rollers 42a and 42b are rotatably mounted on a support-plate (reference sign not appended) that supports the driving mechanism 50. The second guide rollers 42*a* and 42*b* are disposed closer to the pad rotational axis C1 of the transporting device 10 than the second receiving roller 22 is, in the direction perpendicular to the transporting direction D1.

For convenience of explanation, FIG. 5 illustrates the entire portion of the second guide roller 42*a* closer to the pad rotational axis C1 than the second receiving roller 22. However, actually, the second guide roller 42*a* partially overlaps the second receiving roller 22 when viewed in the transporting direction D1 as illustrated in FIG. 6. The same can be said for the second guide roller 42*b*.

Figure 9:
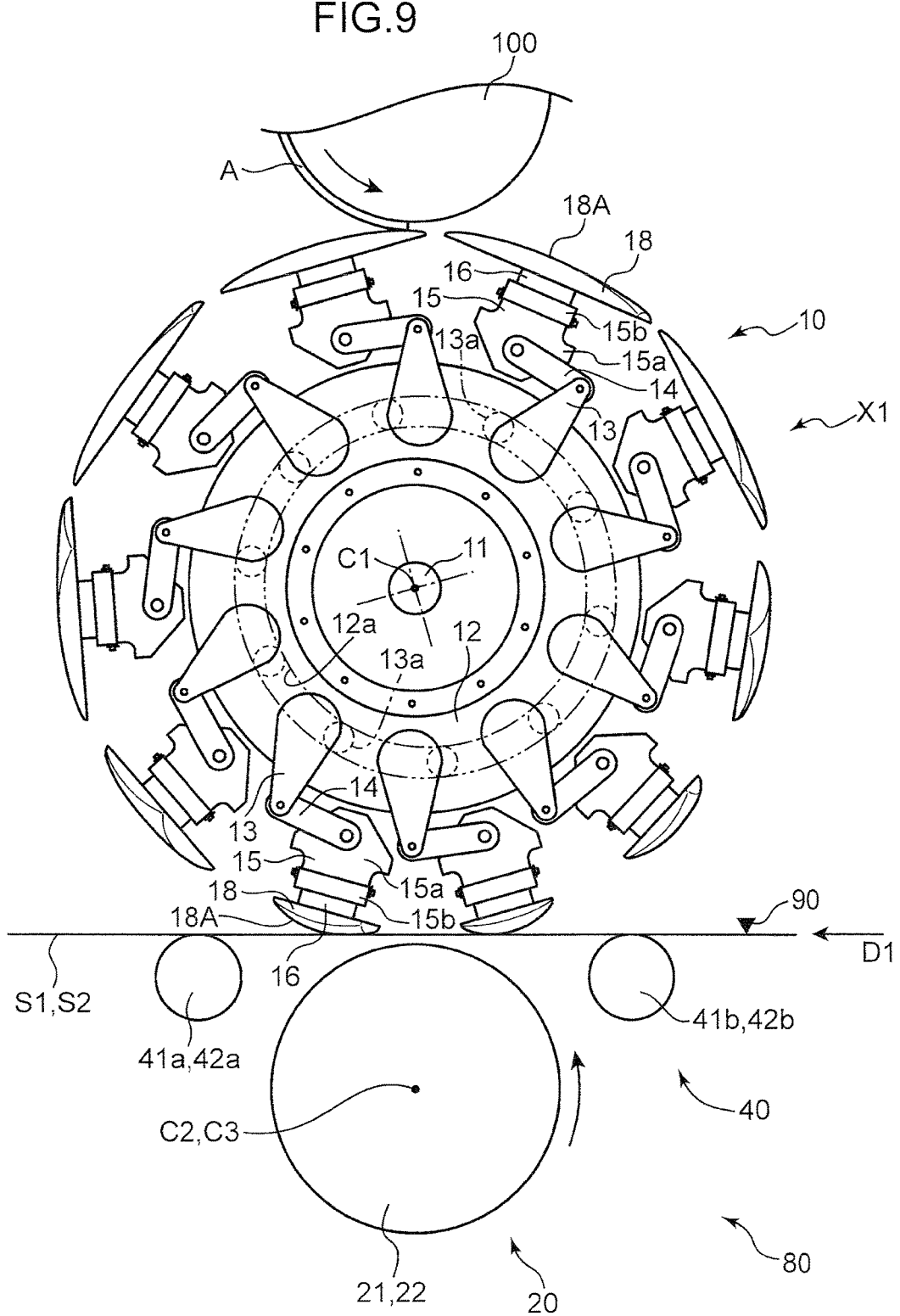
FIG. 9 is a front view illustrating a schematic configuration of a transport unit and a transfer roller according to the embodiment, where none of the pads is at the receiving position nor at the transfer position.

FIG. 9 illustrates the transporting device 10 where the pad 18 is about to reach the transfer position E2, and the receiving unit 80 that receives the absorbent body A from the transporting device 10. As illustrated in FIG. 9, when the pad 18 has not yet reached the transfer position E2, the sheets S1 and S2 extend straight along the transporting direction D1, with the sheet S1 touching the outer circumferential surfaces, facing the transporting device 10, of the first guide rollers 41*a* and 41*b* and the sheet S2 touching the outer circumferential surfaces, facing the transporting device 10, of the second guide rollers 42*a* and 42*b*. Thus, the sheets S1 and S2 are away from the first and second receiving rollers 21 and 22, respectively, when the pad 18 is not at the transfer position E2.

As the transporting device 10 rotates the pad 18 from a position other than the transfer position E2 as illustrated in FIG. 9 to the transfer position E2 as illustrated in FIG. 2, the holding surface 18A of the pad 18 pushes the sheet S1 (S2) to cause the portion of the sheet S1 (S2) between the first guide rollers 41*a* and 41*b* (second guide rollers 42*a* and 42*b*) in the transporting direction D1 to curve toward the first receiving roller 21 (second receiving roller 22). The sheet S1 (S2) thereby contacts the first receiving roller 21 (second receiving roller 22), and thus the sheet S1 (S2) and the absorbent body A are sandwiched between the first receiving roller 21 (second receiving roller 22) and the holding surface 18A of the pad 18.

First, in the transport unit X1, the pad 18 of the transporting device 10 receives the absorbent body A from the transfer roller 100 at the receiving position E1 to hold the absorbent body A on the holding surface 18A. Then, the pad 18, with the absorbent body A received on the holding surface 18A at the receiving position E1, rotates about the pad rotational axis C1 to reach the transfer position E2. With this rotation, the pad 18 turns 90 degrees about an axis extending in a radial direction of the pad rotational axis C1. The pad 18 just about to reach the transfer position E2 rotates while pushing the sheets S1 and S2, conveyed straight along the transporting direction D1 by the guide mechanism 40, against the first and second receiving rollers 21 and 22.

The pad 18 reaches the transfer position E2 to sandwich the sheets S1 and S2 and the absorbent body A between the pad 18 and the first and second receiving rollers 21 and 22. The absorbent body A is thereby joined to the sheets S1 and S2 so as to extend from the sheets S1 to S2.

Then, the pad 18 that has transferred the absorbent body A to the sheets S1 and S2 rotates about the pad rotational axis C1 to reach the receiving position E1. With the rotation, the pad 18 turns 90 degrees about the axis extending in a radial direction of the pad rotational axis C1 to return to the initial position at the receiving position E1. The joint assembly formed by joining the absorbent body A to the sheets S1 and S2 at the transfer position E2 is conveyed to the downstream of the transporting direction D1. In the downstream, a predetermined process is performed on the joint assembly.

As described above, in the transport unit X1, when the pad 18 is at the transfer position E2, the distances from the pad rotating shaft 11 to the first and second sloped surfaces 18*a* and 18*b* included in the holding surface 18A decrease toward the first and second ends 181 and 182, which are the ends of the pad 18 in the direction in which the pad rotating shaft 11 extends. Therefore, when the pad 18 is at the transfer position E2, the circumferential speeds on the first and second sloped surfaces 18*a* and 18*b* decrease toward the first and second ends 181 and 182, which are the ends of the pad 18 in the direction in which the pad rotating shaft 11 extends. In the transport unit X1, the first receiving roller 21 (second receiving roller 22) has a diameter decreasing from the proximal end 21A (22A) toward the distal end 21B (22B) along the first rotational axis C2 (second rotational axis C3), so that the circumferential speed decreases from the proximal end 21A (22A) toward the distal end 21B (22B). The first receiving roller 21 sandwiches the sheet S10 and the absorbent body A between the first sloped surface 18*a* and the first receiving roller with the distal end 21B positioned on the side of the first end 181 of the holding surface 18A, and the second receiving roller 22 sandwiches the sheet S10 and the absorbent body A between the second sloped surface 18*b* and the second receiving roller with the distal end 22B positioned on the side of the second end 182 of the holding surface 18A. In this manner, the difference in circumferential speed between the first curved surface 18*a* (second curved surface 18*b*) and the first receiving roller 21 (second receiving roller 22) is kept small, and thereby forming of crinkles on the absorbent body A or the sheet S10 during joining of the absorbent body A to the sheet S10 is prevented.

Moreover, in the transport unit X1, the first rotational axis C2 (second rotational axis C3) is inclined along the inclination of the first sloped surface 18*a* (second sloped surface 18*b*) to further prevent a large difference in circumferential speed between the first sloped surface 18*a* (second sloped surface 18*b*) and the first receiving roller 21 (second receiving roller 22).

Moreover, in the transport unit X1, the front sheet S1 and the absorbent body A are sandwiched between the first sloped surface 18*a* and the first receiving roller 21 and the rear sheet S2 and the absorbent body A are sandwiched between the second sloped surface 18*b* and the second receiving roller 22, thereby connecting the front sheet S1 to the rear sheet S2 via the absorbent body A without forming crinkles on the absorbent body A or the sheets S1 and S2.

Moreover, the transport unit X1 includes the auxiliary roller 30 for pushing the absorbent body A, positioned at the middle surface 18*c*, onto the middle surface 18*c* which is farther apart from the pad rotating shaft 11 than the first sloped surface 18*a* and the second sloped surface 18*b* and therefore likely to generate the maximum centrifugal force. This prevents the absorbent body A positioned on the middle surface 18*c* from being joined to the sheets S1 and S2 with a gap between the absorbent body A and the middle surface 18*c*, and thereby forming of crinkles on the absorbent body A or the sheets S1 and S2 is further prevented.

Furthermore, in the transport unit X1, the outer circumferential member 21*b* (22*b*) of the first receiving roller 21 (second receiving roller 22) is divided into the first member 21*c* (22*c*) and the second member 21*d* (22*d*). The first and second members 21*c* and 21*d* are detachably attached on both sides, with respect to a direction intersecting the first rotational axis C2, of the shaft member 21*a*, and the first and second members 22*c* and 22*d* are detachably attached on both sides, with respect to a direction intersecting the second rotational axis C3, of the shaft member 22*a*. Thus, for example, the outer circumferential members 21*b* and 22*b* can easily be replaced when the outer circumferential members 21*b* and 22*b* wear by making contact with the sheets S1 and S2.

Furthermore, in the transport unit X1, the guide mechanism 40 guides the sheets S1 and S2 to be transported so that the sheets S1 and S2 are not in contact with the first and second receiving rollers 21 and 22 while the pad 18 is at a position other than the transfer position E2. This prevents wear of the outer circumferential members 21*b* and 22*b* of the first and second receiving rollers 21 and 22 caused by the first and second receiving rollers 21 and 22 making contact with the sheets S1 and S2 for a long period of time.

It should be construed that the embodiment is described above totally by means of illustration, not by means of limitation. The scope of the present invention is determined not by the description on the embodiment but by the claims. Modifications equivalent to or within the scope of the claims all fall within the scope of the present invention.

For example, in the transport unit X1 according to the embodiment, the sheet S10 is composed of two independent sheets, which are the front sheet S1 and the rear sheet S2. However, the sheet S10 may be composed of a single sheet.

In the transport unit X1 according to the embodiment, the first and second sloped surfaces 18*a* and 18*b* each has a curved shape. However, the shapes of the first and second sloped surfaces 18*a* and 18*b* are not limited to a curved shape. The first and second sloped surfaces 18*a* and 18*b* may have any shapes such that the distances from the pad rotating shaft 11 to the first and second sloped surfaces 18*a* and 18*b* decrease toward the first and second ends 181 and 182 so that the absorbent body A is smoothly received from the transfer roller 100 at the receiving position E1. The first and second sloped surfaces 18*a* and 18*b* each may have a flat shape.

In the transport unit X1 according to the embodiment, the middle surface 18*c* has a curved shape. However, the shape of the middle surface is not limited to a curved shape. For example, the middle surface 18*c* may have a flat shape extending in the longitudinal direction of the pad 18 between the inner edges of the first and second sloped surfaces 18*a* and 18*b*.

In the transport unit X1 according to the embodiment, the guide mechanism 40 includes the first guide rollers 41*a* and 41*b* disposed on both sides of the first receiving roller 21 in the transporting direction D, and the second guide rollers 42*a* and 42*b* disposed on both sides of the second receiving roller 22 in the transporting direction D. However, the guide mechanism 40 is not limited to the above. The guide mechanism 40 may have any configuration that can guide the sheet S1 (S2) to be conveyed such that the sheet S1 (S2) is away from the first receiving roller 21 (second receiving roller 22) while the pad 18 is at a position other than the transfer position E2. The number and dispositions of the guide rollers included in the guide mechanism 40 are not particularly limited. The guide mechanism 40 may not include a guide roller but may include an unrotatable guiding member.

In the transport unit X1 according to the embodiment, the outer circumferential member 21*b* (22*b*) of the first receiving roller 21 (second receiving roller 22) is divided into the first member 21*c* (22*c*) and the second member 21*d* (22*d*). However, the present invention is not limited to the embodiment. For example, only the outer circumferential member 21*b* of the first receiving roller 21 may be divided into the first member 21*c* and the second member 21*d* while the entire outer circumferential member 21*b* of the second receiving roller 22 forms a single part.

The embodiment will now schematically be described.

A transport unit according to an aspect of the present invention is a transport unit that conveys a first transportation object onto a second transportation object and joins the first transportation object to the second transportation object. The transport unit includes: a transporting device including a pad rotating shaft, and a pad having a holding surface that faces radially outwardly with respect to the pad rotating shaft and is capable of holding the first transportation object, the transporting device being configured to rotate the pad about the pad rotating shaft and to turn the pad about an axis extending in a radial direction of the pad rotating shaft while the pad is rotated from a receiving position where the pad receives the first transportation object to a transfer position where the pad transfers the first transportation object onto the second transportation object; and a receiving roller that, when the pad rotates and comes to the transfer position, rotates while sandwiching the first transportation object and the second transportation object between the holding surface of the pad and the receiving roller to join the first transportation object to the second transportation object and guide the second transportation object to a predetermined direction. The holding surface includes a first sloped surface and a second sloped surface, the first sloped surface and the second sloped surface being such that, when the pad is at the transfer position, a distance from the pad rotating shaft to the first sloped surface decreases toward a first end along the pad rotating shaft, while a distance from the pad rotating shaft to the second sloped surface decreases toward a second end along the pad rotating shaft. The receiving roller includes a first receiving roller and a second receiving roller. The first receiving roller is disposed such that an outer diameter of the first receiving roller decreases from a proximal end to a distal end along a first rotational axis which is a rotation center of the first receiving roller, and the distal end of the first receiving roller is positioned on the side of the first end of the holding surface to sandwich the first transportation object and the second transportation object between the first sloped surface and the first receiving roller when the pad is at the transfer position, and the second receiving roller is disposed such that an outer diameter of the second receiving roller decreases from a proximal end to a distal end along a second rotational axis which is a rotation center of the second receiving roller, and the distal end of the second receiving roller is positioned on the side of the second end of the holding surface to sandwich the first transportation object and the second transportation object between the second sloped surface and the second receiving roller when the pad is at the transfer position.

In the transport unit, when the pad is at the transfer position, the distance from the pad rotating shaft to the first sloped surface (second sloped surface) included in the holding surface decreases toward the first end (second end), which is an end of the pad in the direction in which the pad rotating shaft extends. Therefore, when the pad is at the transfer position, the circumferential speed of the first sloped surface (second sloped surface) decreases toward the first end (second end), which is an end of the pad in the direction in which the pad rotating shaft extends. In the transport unit described above, the first receiving roller (second receiving roller) has a diameter decreasing from the proximal end toward the distal end along the first rotational axis (second rotational axis), which is the rotation center of the first receiving roller (second receiving roller), so that the circumferential speed of the first receiving roller (second receiving roller) decreases from the proximal end toward the distal end. The first receiving roller sandwiches the first transportation object and the second transportation object between the first sloped surface and the first receiving roller with the distal end of the first receiving roller positioned on the side of the first end of the holding surface, and the second receiving roller sandwiches the first transportation object and the second transportation object between the second sloped surface and the second receiving roller with the distal end of the second receiving roller positioned on the side of the second end of the holding surface. Compared to first and second rollers having a cylindrical shape, the difference in circumferential speed between the first sloped surface (second sloped surface) and the first receiving roller (second receiving roller) can be kept small, and thereby forming of crinkles on the first transportation object and the second transportation object during joining of the first transportation object to the second transportation object can further be prevented.

The first and second sloped surfaces of the pad of the transport unit may not necessarily have a flat shape but may have a curved shape.

It is preferable that the first receiving roller is disposed to face the first sloped surface with the first rotational axis inclined along an inclination of the first sloped surface, and the second receiving roller is disposed to face the second sloped surface with the second rotational axis inclined along an inclination of the second sloped surface.

In the transport unit, the first rotational axis (second rotational axis) is inclined along the inclination of the first sloped surface (second sloped surface), so that the difference in circumferential speed between the first sloped surface (second sloped surface) and the first receiving roller (second receiving roller) is kept small.

It is preferable that the second transportation object includes a first transportation element and a second transportation element, the transporting device conveys the first transportation object so that the first transportation object extends from the first transportation element to the second transportation element when the pad is at the transfer position, the first receiving roller is disposed so as to sandwich the first transportation object and the first transportation element between the first sloped surface and the first receiving roller when the pad is at the transfer position, and the second receiving roller is disposed so as to sandwich the first transportation object and the second transportation element between the second sloped surface and the second receiving roller when the pad is at the transfer position.

In the transport unit, the first transportation object and the first transportation element are sandwiched between the first sloped surface and the first receiving roller while the first transportation object and the second transportation element are sandwiched between the second sloped surface and the second receiving roller, thereby connecting the first transportation element to the second transportation element by the first transportation object without forming crinkles on the first transportation object or the second transportation object.

It is preferable that the holding surface includes a middle surface provided between the first sloped surface and the second sloped surface in a direction along the pad rotating shaft when the pad is at the transfer position, a distance from the pad rotating shaft to the middle surface being longer than a distance from the pad rotating shaft to the first sloped surface and a distance from the pad rotating shaft to the second sloped surface, and the transport unit further includes an auxiliary roller that is positioned between the first receiving roller and the second receiving roller in a direction along the pad rotating shaft and that rotates while sandwiching the first transportation object between the middle surface and the auxiliary roller when the pad rotates and comes to the transfer position.

The transport unit includes the auxiliary roller for pushing a portion of the first transportation object, positioned at the middle surface, onto the middle surface which is farther apart from the rotating shaft than the first sloped surface and the second sloped surface and therefore likely to generate the maximum centrifugal force. This prevents the first transportation object from being joined to the first transportation element and the second transportation element with a gap between the portion of the first transportation object and the middle surface, and thereby forming of crinkles on the first transportation object or on the second transportation object can further be prevented.

It is preferable that the first receiving roller includes a shaft member rotatable about the first rotational axis, and an outer circumferential member that surrounds a circumference of the shaft member and sandwiches the first transportation object and the second transportation object between the holding surface and the first receiving roller, the outer circumferential member includes a first member and a second member, the outer circumferential member is divided into the first member and the second member in a direction perpendicular to the first rotational axis, and the first member and the second member are detachably attached on both sides of the shaft member in a direction intersecting the first rotational axis.

In the transport unit, the outer circumferential member of the first receiving roller is divided into the first member and the second member which are detachably attached on both sides of the shaft member. This allows easy replacement of the first and second members when the first and second members wear by making contact with the second transportation object, for example.

It is preferable that the transport unit further includes a guide mechanism that is provided on opposite side of the transporting device with respect to the second transportation object and is configured to guide the second transportation object such that the second transportation object is away from the receiving roller when the pad is at a position other than the transfer position, and the second transportation object pushed by the holding surface of the pad at the transfer position makes contact with the receiving roller.

In the transport unit, the guide mechanism guides the second transportation object to be transported so that the first transportation object is not in contact with the second transportation object while the pad is at a position other than the transfer position. This prevents wear of the receiving roller caused by the second transportation object making contact with the receiving roller for a long period of time.

A method for manufacturing a disposable wearing article using a transport unit according to an aspect of the present invention uses the transport unit according to any one of claims 1 to 5 to manufacture a disposable wearing article including a waist part that is to be positioned around a waist of a wearer and a crotch part that is to be positioned at a crotch of the wearer. The method includes: a sheet transporting step of conveying a waist sheet along a longitudinal direction of the waist sheet by using the transport unit, the waist sheet corresponding to the second transportation object and being to form the waist part; a crotch section element joining step of transporting a crotch section element that corresponds to the first transportation object and is provided to form a portion corresponding to the crotch part onto the waist sheet and joining the crotch section element to the waist sheet to form a joint assembly; a folding step of folding the joint assembly in a width direction perpendicular to the longitudinal direction; a side sealing step of joining overlapping portions of the waist sheet on both sides with respect to the crotch section element in the longitudinal direction to form side seals; and a cutting step of cutting the waist sheet so that the side seals remain on both the sides with respect to the crotch section element in the longitudinal direction to form a disposable wearing article.

In the method for manufacturing a disposable wearing article, the crotch section element is conveyed onto the waist sheet and the crotch section element is joined to the waist sheet using the transport unit according to the present invention, so that forming of crinkles on the crotch part or the waist part of the disposable wearing article is prevented.

The invention claimed is:

1. A transport unit configured to convey a first transportation object onto a second transportation object and join the first transportation object to the second transportation object, the transport unit comprising:
a transporting device including a pad rotating shaft configured to rotate about a pad rotational axis, and a pad having a holding surface that faces radially outwardly with respect to the pad rotating shaft and is configured to hold the first transportation object, the transporting device being configured to rotate the pad about the pad rotating shaft and turn the pad about an axis extending in a radial direction of the pad rotating shaft while the pad is rotated from a receiving position where the pad receives the first transportation object to a transfer position where the pad transfers the first transportation object onto the second transportation object; and
a receiving roller that is configured to, when the pad rotates and comes to the transfer position, rotate while sandwiching the first transportation object and the second transportation object between the holding surface of the pad and the receiving roller, to join the first transportation object to the second transportation object and guide the second transportation object to a predetermined direction,
wherein:
the holding surface includes a first sloped surface and a second sloped surface, the first sloped surface and the second sloped surface being configured such that, when the pad is at the transfer position, a distance from the pad rotational axis to the first sloped surface decreases toward a first end along the pad rotating shaft, and a distance from the pad rotational axis to the second sloped surface decreases toward a second end along the pad rotating shaft;
the receiving roller includes a first receiving roller and a second receiving roller;
an outer diameter of the first receiving roller decreases from a proximal end of the first receiving roller to a distal end of the first receiving roller along a first rotational axis which is a rotation center of the first receiving roller, and the distal end of the first receiving roller is positioned on a side of the first end of the holding surface to sandwich the first transportation object and the second transportation object between the first sloped surface and the first receiving roller when the pad is at the transfer position; and an outer diameter of the second receiving roller decreases from a proximal end of the second receiving roller to a distal end of the second receiving roller along a second rotational axis which is a rotation center of the second receiving roller, and the distal end of the second receiving roller is positioned on a side of the second end of the holding surface to sandwich the first transportation object and the second transportation object between the second sloped surface and the second receiving roller when the pad is at the transfer position.

2. The transport unit according to claim 1, wherein:
a distance from the pad rotational axis to the first rotational axis of the first receiving roller decreases from the proximal end of the first receiving roller to the distal end of the first receiving roller such that, when the pad is at the transfer position, the first receiving roller faces the first sloped surface; and
a distance from the pad rotational axis to the second rotational axis of the second receiving roller decreases from the proximal end of the second receiving roller to the distal end of the second receiving roller such that, when the pad is at the transfer position, the second receiving roller faces the second sloped surface.

3. The transport unit according to claim 1, wherein:
the second transportation object includes a first transportation element, and a second transportation element;
the transporting device conveys is configured to convey the first transportation object so that the first transportation object extends from the first transportation element to the second transportation element when the pad is at the transfer position;
the first receiving roller is configured to sandwich the first transportation object and the first transportation element between the first sloped surface and the first receiving roller when the pad is at the transfer position; and
the second receiving roller is configured to sandwich the first transportation object and the second transportation element between the second sloped surface and the second receiving roller when the pad is at the transfer position.

4. The transport unit according to claim 3, wherein:
the holding surface includes a middle surface between the first sloped surface and the second sloped surface in a direction along the pad rotating shaft, and when the pad is at the transfer position, a distance from the pad rotational axis to the middle surface is longer than a distance from the pad rotational axis to the first sloped surface and a distance from the pad rotational axis to the second sloped surface;
the transport unit further comprising:
an auxiliary roller between the first receiving roller and the second receiving roller in the direction along the pad rotating shaft, the auxiliary roller being configured to rotate while sandwiching the first transportation object between the middle surface and the auxiliary roller when the pad rotates and comes to the transfer position.

5. The transport unit according to claim 1, wherein:
the first receiving roller includes a shaft member configured to rotate about the first rotational axis, and an outer circumferential member that surrounds a circumference of the shaft member and sandwiches the first transportation object and the second transportation object between the holding surface and the first receiving roller;

the outer circumferential member includes a first member and a second member, the outer circumferential member being divided into the first member and the second member in a direction perpendicular to the first rotational axis; and the first member and the second member are detachably attached on both sides of the shaft member with respect to a direction intersecting the first rotational axis.

6. The transport unit according to claim 1, further comprising:

a guide mechanism on an opposite side of the transporting device with respect to the second transportation object, the guide mechanism being configured to guide the second transportation object such that the second transportation object is away from the receiving roller when the pad is at a position other than the transfer position, and the second transportation object pushed by the holding surface of the pad at the transfer position makes contact with the receiving roller.

7. A method for manufacturing a disposable wear article including a waist part that is to be positioned around a waist of a wearer and a crotch part that is to be positioned at a crotch of the wearer, the method using the transport unit according to claim 1, and the method comprising:

conveying a waist sheet along a longitudinal direction of the waist sheet, the waist sheet corresponding to the second transportation object and forming the waist part;

conveying a crotch section element that corresponds to the first transportation object and forms a portion corresponding to the crotch part onto the waist sheet and joining the crotch section element to the waist sheet to form a joint assembly using the transport unit;

folding the joint assembly in a width direction perpendicular to the longitudinal direction;

joining overlapping portions of the waist sheet on both sides with respect to the crotch section element in the longitudinal direction to form side seals; and cutting the waist sheet so that the side seals remain on both of the sides with respect to the crotch section element in the longitudinal direction to form the disposable wear article.

* * * * *